US006248580B1

(12) United States Patent
Spain et al.

(10) Patent No.: US 6,248,580 B1
(45) Date of Patent: Jun. 19, 2001

(54) PROCESS FOR THE BIODEGRADATION OF DINITROTOLUENE

(75) Inventors: Jim C. Spain; Shirley F. Nishino, both of Panama City, FL (US); Urs Lendenmann, Rehetobel (CH)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/220,220

(22) Filed: Dec. 23, 1998

(51) Int. Cl.[7] .................................................... C12S 13/00
(52) U.S. Cl. ........................................ 435/262.5; 435/262
(58) Field of Search ................................. 435/262, 262.5

(56) References Cited

U.S. PATENT DOCUMENTS

| | | |
|---|---|---|
| 4,992,174 | 2/1991 | Caplan et al. . |
| 5,455,173 | 10/1995 | Crawford et al. . |
| 5,478,743 | 12/1995 | Perkins et al. . |
| 5,616,162 | 4/1997 | Crawford et al. . |

OTHER PUBLICATIONS

Nishino, S. F. et al., Abstract, ASM (1998) vol. 98, p. 435. 98th General Meeting of the American Society for Microbiology Atlanta, Georgia, USA May 17–21, 1998.*
Nishino et al., Man. Environ. Microbiol, (1997). pp. 776–783.*
Nishino et al., Abstract, ASM (1997) vol. 97, No. 0, p. 513. 97th General Meeting of the American Society for Microbiology Miami Beach, Florida, USA May 4–8, 1997.*
Nishino et al., Abstract ASM, 96th General Meeting og the American Society for Microbiology New Orleans, Louisiana, USA May 19–23, 1996; vol. 96, No. 8, pp. 452.*
Lendehmann et al., Environmental Science & Technology, (Jan.,1998) vol. 32, No. 1, pp. 82–87.*
Heinze et al., Acta Hydrochimica et Hydrobiologica, (1995) vol. 23, No. 6, pp. 254–263.*
Davis et al., Water Res, (1981) 15 (9), 1125–1127.*
Khan et al., Abstract, ASM 92nd General Meeting of the American Society for Microbiology, New Orleans, Louisiana, USA, May 26–30, 1992. (1992) 92 (0), 358.*
U. Lendenmann, J.C. Spain and B.F. Smets, Simultaneous Biodegradation of 2,4–Dinitrotoluene and 2,6–Dinitrotoluene in an Aerobic Fluidized–Bed Biofilm Reactor, Environmental Science & Technology, vol. 32, No. 1, 1998 (No month given).

* cited by examiner

*Primary Examiner*—Irene Marx
(74) *Attorney, Agent, or Firm*—Charles E. Bricker; Thomas L. Kundert

(57) ABSTRACT

Dinitrotoluene present as a contaminant in a sample, is degraded by the steps of (a) providing a sample comprising dinitrotoluene; (b) adding to the sample at least one bacterial strain capable of degrading at least one dinitrotoluene isomer under aerobic conditions; (c) producing aerobic conditions in the sample; and (d) maintaining the aerobic conditions in the sample for a time that is sufficient for the bacteria to degrade said dinitrotoluene. In one embodiment, at least one bacterial strain capable of degrading the 2,4-dinitrotoluene isomer under aerobic conditions is added to the sample. In another embodiment, at least one bacterial strain capable of degrading the 2,6-dinitrotoluene isomer under aerobic conditions is added to the sample. In yet another embodiment, at least one bacterial strain capable of degrading both the 2,4-dinitrotoluene isomer and the 2,6-dinitrotoluene isomer under aerobic conditions is added to the sample. In a further embodiment, a mixed culture of bacteria that degrade both isomers under aerobic conditions is added to the sample.

2 Claims, 3 Drawing Sheets

PROCESS FOR THE BIODEGRADATION OF DINITROTOLUENE

RIGHTS OF THE GOVERNMENT

The invention described herein may be manufactured and used by or for the Government of the United States for all governmental purposes without the payment of any royalty.

BACKGROUND OF THE INVENTION

The present invention relates to the biodegradation of dinitrotoluene in water and soils using microorganisms.

Dinitrotoluenes (DNT) are intermediates in the production of the explosive 2,4,6-trinitrotoluene (TNT) and precursors of toluenediisocyanate, which is used in the manufacture of polyurethane foams. Typically, synthesis yields 76% 2,4-DNT, 19% 2.6-DNT and small amounts of other isomers. Disposal practices associated with TNT manufacturing dating back to World Wars I and II, have resulted in an enormous contamination problem at ammunition production and handling facilities worldwide. The estimated cost for cleanup of defense sites in the United States alone is $2.66 billion. Explosives contamination just at the active installations is estimated to include 750,000 cubic yards of soil and 530 billion gallons of groundwater. Although TNT is no longer produced in the U.S., the current worldwide production of DNT is 2.7 billion pounds per year, some of which ends up in wastewater discharged from DNT manufacturing plants. Both 2,4- and 2,6-DNT are listed as U.S. Environmental Protection Agency (EPA) priority pollutants in, for example, the Clean Water Act and the Safe Drinking Water Act.

2,4-DNT and 2,6-DNT exhibit acute toxicity and low level carcinogenicity. The 14-day $LC_{50}$ for guppy (*Poecilia reticulata*) of 2,4-DNT (69 $\mu$M, 12.5 mg/L) and of 2,6-DNT (98 $\mu$M, 18 mg/L) indicate aquatic toxicity at low concentrations. EPA treatment standards are 0.32 mg/L for 2,4-DNT and 0.55 mg/L for 2,6-DNT.

Because of the hazards DNT, TNT, and their transformation products pose for drinking water supplies, efforts have been undertaken to understand the fate of the compounds in the environment. DNT may undergo a variety of transformations undeir environmental conditions. One of the most commonly reported transformations has been nonspecific reduction of one or more of the nitro groups attached to the benzene ring to form aminonitro- and diamino-toluenes via hydroxylamino- and nitroso-intermediates. It has also been reported that acetylation is a significant reaction of arylamines produced by reduction of DNT. The reduced intermediates are believed to be responsible for much of the toxicity attributed to DNT. The nonspecific reductions are generally the result of cometabolism, a process in which the transformation of the chemical is incidental to the degradation of another chemical. The organism does not normally derive any metabolic benefit from cometabolic transformations and cannot grow on the cometabolized compound. Cometabolic systems are difficult to control and do not completely destroy the contaminants. Continued transformation of the compound requires input of another carbon source to provide energy to drive the reaction and to keep the necessary enzymes induced.

Mineralization on the other hand allows the organism to use the contaminant as a source of carbon and energy for growth. In mineralization, degradation of the compound goes beyond one or two transformation steps to the cleavage of the carbon backbone, so that the organism derives energy and structural material from the compound, and releases small inorganic molecules, predominantly water and $CO_2$.

Because the bacteria derive a benefit, mineralization of the contaminants results in a controllable self sustaining process. Mineralization of 2,4- and 2,6-DNT at concentrations up to 10 mg/L by natural river water populations collected downstream of a TNT-manufacturing plant, following lag periods of up to 3 weeks, has been reported. Neither the pathways involved nor the organisms responsible for the mineralization were characterized. Based upon rate studies, it was concluded that at low DNT concentrations, microbial degradation played only a minor role in the removal of DNT from surface waters. Mineralization of 2,4- and 2,6-DNT by populations of microorganisms indigenous to a shallow aquifer at an explosives-contaminated site have also been reported. In all cases, DNT concentrations were less than 20 mg/L. After 28 days, 28% of initial 2,4-DNT was mineralized, 20% was undegraded, 28% was recovered as aminonitrotoluenes and 24% was in unidentified metabolites. For 2,6-DNT the percentages were 8, 67, 14, and 11%, respectively. The picture that emerged from these reports of mineralization of DNT by natural assemblages was one of slow mineralization, which, even under aerobic conditions, lost out to competition from nonspecific transformation reactions.

Extensive research has focused on the microbial transformation of nitroaromatic compounds and how contaminated sites can be cleaned up through bioremediation. Removal of DNT by microbial cultures has been reported; however as stated above, processes used to date have generally been cometabolic, and the microorganisms involved did not use DNT as a growth source. Mixed cultures that cometabolize 2,4-DNT under anaerobic conditions when ethanol is provided as the primary carbon and energy source have been reported. In these systems aromatic amines accumulated. The major strength of the anaerobic system is the ability to transform 2,4-DNT in the presence of other carbon sources.

Composting systems for explosives-contaminated soils have received much attention in recent years, however no composting systems have been developed specifically for DNT. At present, composting presents two major drawbacks: (1) generally, no more than 10 to 30% of the compost pile can be made up of the contaminated soil, resulting in an increase in the amount of product that must eventually be landfilled; and (2) despite concerted efforts, residual toxicity of finished compost is still undetermined. It has been reported that fungi mineralize DNT under ligninolytic conditions. However, the ligninolytic systems do not appear to be involved in the initial reduction of DNT, which requires live mycelia. The ligninolytic system is necessary for the mineralization of the aminoaromatic products of DNT reduction. The limiting factor in the fungal systems has been the toxicity of DNT at concentrations found in contaminated soils.

Bacterial strains capable of degrading 2,4-DNT have been isolated and characterized and the degradation pathway determined. The pathway proceeds through dioxygenation of 2,4-DNT to 4-methyl-5-nitrocatechol; monooxygenation of 4-methyl-5-nitrocatechol then yields 2-hydroxy-5-methylquinone which is subsequently reduced to 2,4,5-trihydroxytoluene prior to ring cleavage. 2,4-DNT-degrading bacteria are not, however, able to degrade the mixtures of DNT isomers (80:20 2,4-DNT:2,6-DNT) found at contaminated sites, and the presence of high concentrations of 2,6-DNT can inhibit 2,4-DNT degradation. Cultures grown on 2,4-DNT, when incubated in the presence of mixtures of 2,4-DNT and 2,6-DNT, are inhibited in the degradation of 2,4-DNT, and 4-methyl-5-nitrocatechol accumulates in the culture fluid, as well as a metabolite from 2,6-DNT.

It is an object of the present invention to provide a process for the biodegradation of samples contaminated with a mixture of 2,4-dinitrotoluene and 2,6-dinitrotoluene.

Other objects, aspects and advantages of the present invention will be apparent to those skilled in the art from a reading of the following detailed disclosure of the invention.

SUMMARY OF THE INVENTION

In accordance with the present invention there is provided a method for biodegrading dinitrotoluene present as a contaminant in a sample, comprising the steps of (a) providing a sample comprising dinitrotoluene; (b) adding to the sample at least one bacterial strain capable of degrading at least one dinitrotoluene isomer under aerobic conditions; (c) producing aerobic conditions in the sample; and (d) maintaining the aerobic conditions in the sample for a time that is sufficient for the bacteria to degrade said dinitrotoluene.

Thus, in one embodiment of the invention at least one bacterial strain capable of degrading the 2,4-dinitrotoluene isomer under aerobic conditions is added to the sample. In another embodiment of the invention at least one bacterial strain capable of degrading the 2,6-dinitrotoluene isomer under aerobic conditions is added to the sample. In yet another embodiment of the invention at least one bacterial strain capable of degrading both the 2,4-dinitrotoluene isomer and the 2,6-dinitrotoluene isomer under aerobic conditions is added to the sample. In a further embodiment of the invention a mixed culture of bacteria that degrades both isomers under aerobic conditions is added to the sample.

DETAILED DESCRIPTION OF THE INVENTION

Figure 1:
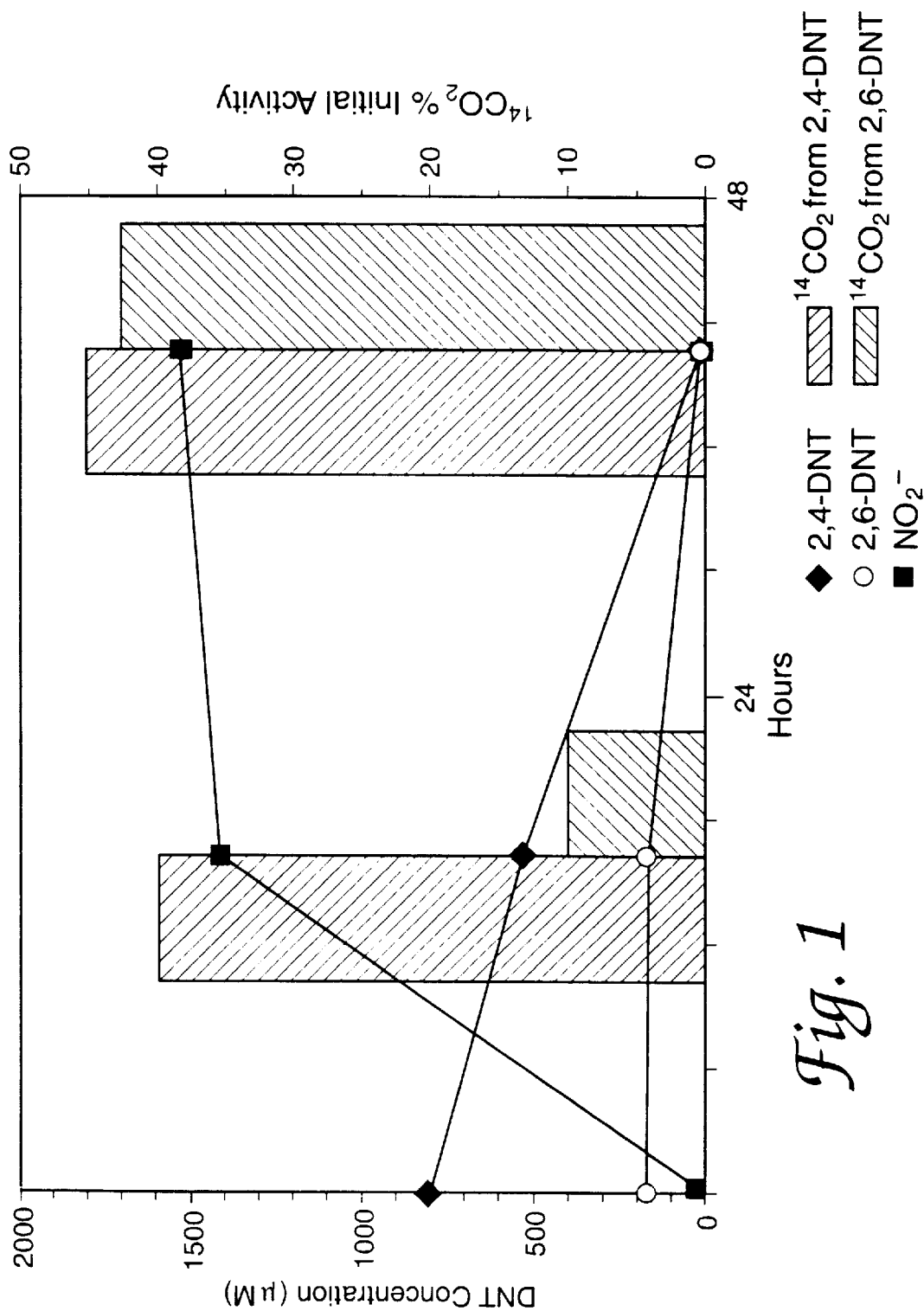
FIG. 1 shows the simultaneous mineralization of 2,4-DNT and 2,6-DNT in a batch soil slurry reactor.

Inocula were obtained from a variety of DNT-contaminated soils, groundwater, and industrial waste treatment streams. The inocula were used in enrichment cultures containing either 2,4- or 2,6-DNT as the sole carbon, nitrogen and energy source. After enrichment, specific strains of bacteria were isolated and tested for the ability to release nitrite from and grow on 2,4-DNT or 2,6-DNT. Strains which utilize DNT as sole carbon and nitrogen sources have been isolated from four sites in the United States, one site in Canada, 5 sites in Germany and one site in Scotland. None of the 2,6-DNT-degradirg strains isolated from 2,6-DNT enrichments can degrade 2,4-DNT, and none of the 2,4-DNT-degrading strains isolated from 2,4-DNT enrichments can degrade 2,6-DNT.

A single 2,4-DNT degrading strain was combined in a chemostat (250 ml working volume) with 19 strains able to degrade 2,6-DNT along with a culture that had been enriched on 2,6-DNT for 6 months. The enrichment consisted of replacement of 50% of the culture fluid with minimal medium containing 100 $\mu$M 2,6-DNT every 1 to 2 weeks. The original inoculum for the culture was a mixture of DNT-contaminated industrial waste sludges, soils, and ground waters. The chemostat was fed a mixture of 2,4-DNT and 2,6-DNT (81 and 18 mg/L, respectively, in the influent) as the sole carbon, nitrogen and energy source and operated at dilution rates from 0.01 to 0.05 over a 6 month period. At the end of 6 months, 25 ml of the chemostat culture was used to inoculate a fluidized bed biofilm reactor. The fluidized bed biofilm reactor was sampled periodically to isolate bacteria able to grow on DNT. Initial samples yielded isolates able to grow only on 2,4- or 2,6-DNT, but not both. After 3 months of selection, bacteria were isolated that had the ability to use either DNT isomer as a growth substrate. DNT-degrading strains were identified by 16S rDNA analysis. The selected DNT-degrading strains are shown in Table I, below:

TABLE I

| Strain | Species | DNT mineralized | ATCC Designation |
|---|---|---|---|
| JS850 | Burkholderia cepacia | 2,6-DNT | 700448 |
| JS863 | Hydrogenophaga palleronii | 2,6-DNT | 700449 |
| JS872 | Burkholderia cepacia | 2,4-DNT | 700450 |
| JS922 | Burkholderia cepacia | 2,4-DNT, 2,6-DNT | BAA-18 |

Additionally, a strain identified as JS921 was isolated. The original 16S rDNA preparations from JS921 were of too poor a quality to identify the strain, and physiological measures, such as Biolog identification, were also poor. The molecular procedure for that strain was not repeated.

In all strains examined, the initial transformation of 2,6-DNT produced 3-methyl-4-nitrocatechol via a dioxygenase attack similar to that used by 2,4-DNT degrading strains. During the initial dioxygenation, one of the nitro groups is released. The aromatic ring of 3-methyl4-nitrocatechol was opened by a catechol-2,3-dioxygenase. The remaining nitro group was released in as yet undescribed reactions subsequent to ring cleavage.

Degradation of radiolabeled DNT resulted in the release of 39 to 55% of the initial radiolabel as $^{14}CO_2$, as well as release of both nitro groups and an increase in protein, which indicates growth of the bacteria. DNT degrading strains remove DNT from aqueous solutions containing as much as 1 mM DNT (the approximate limit of solubility of DNT in water at room temperature), with or without the presence of soil, and with or without the presence of other non-DNT degrading bacteria.

For the treatment of aqueous solutions contaminated with 2,4-DNT and 2,6-DNT, DNT-degrading bacteria were grown under aerobic conditions in batch or continuous process reactors, including but not limited to reactors that retain biomass formed in the culture by attachment of the bacteria to a carrier material or biomass recycling by cross flow filtration. The process was tested in a bench scale fluid bed biofilm reactor (FBBR) using sand or granular activated carbon as the carrier material.

The following examples illustrate the invention:

EXAMPLE I

Simultaneous Mineralization of 2,4-DNT and 2,6-DNT in a Batch Soil Slurry Reactor Burkholderia cepacia JS872, a 2,4-DNT degrading strain, and Hydrogenopha palleronii JS863, a 2,6-DNT degrading strain, were combined in non-sterile 10% (w/v) soil slurries containing 2,4DNT (800 $\mu$M) and 2,6-DNT (200 $\mu$M). The total volume of soil slurries was 25 ml in 250 ml shake flasks equipped with glass centerwells. Initial biomass of JS872 and JS863 added was 0.36 and 0.40 mg/ml of protein. The soils which were mixed together and passed through a 20 mesh sieve, were from a variety of sources with no history of DNT contamination. Three cultures also received radiolabeled 2,4-DNT, and three received radiolabeled 2,6-DNT. One of each of these cultures was sterilized with $HgCl_2$ (2.5 $\mu$g/ml). Additional flasks with added DNT and radiolabel, but no DNT-degrading strains, were used as controls. 200 $\mu$l of 5N KOH was added to the centerwell of each flask. Flasks were sealed and incubated at 30° C., with shaking at 150 rpm. Daily samples were collected for analysis of 2,4-DNT, 2,6-DNT, $NO_2^-$ and radiolabel in culture fluid, as well as $^{14}CO_2$ trapped in KOH. The KOH was replaced daily. Results are shown in FIG. 1. Both 2,4- and 2,6-DNT became nondetectable in the culture fluid within 48 h. Two mol of nitrite were released per mol of DNT degraded, indicating complete degradation of DNT. Over 40% of the initial radiolabel was trapped as $^4CO_2$, indicating levels of mineralization well within the ncrm for growth substrates. Control cultures released no $NO_2^-$; $^{14}CO_2$ and DNT concentrations in the culture fluids remained unchanged. When Burkholderia cepacia JS922, a strain which can degrade 2,4- and 2,6-DNT simultaneously, was used in soiil slurries during the same experiment, results were similar. This example demonstrates that cultures of specific DNT-degrading strains mineralize high concentrations of DNT within a short time period.

EXAMPLE II

Figure 2:
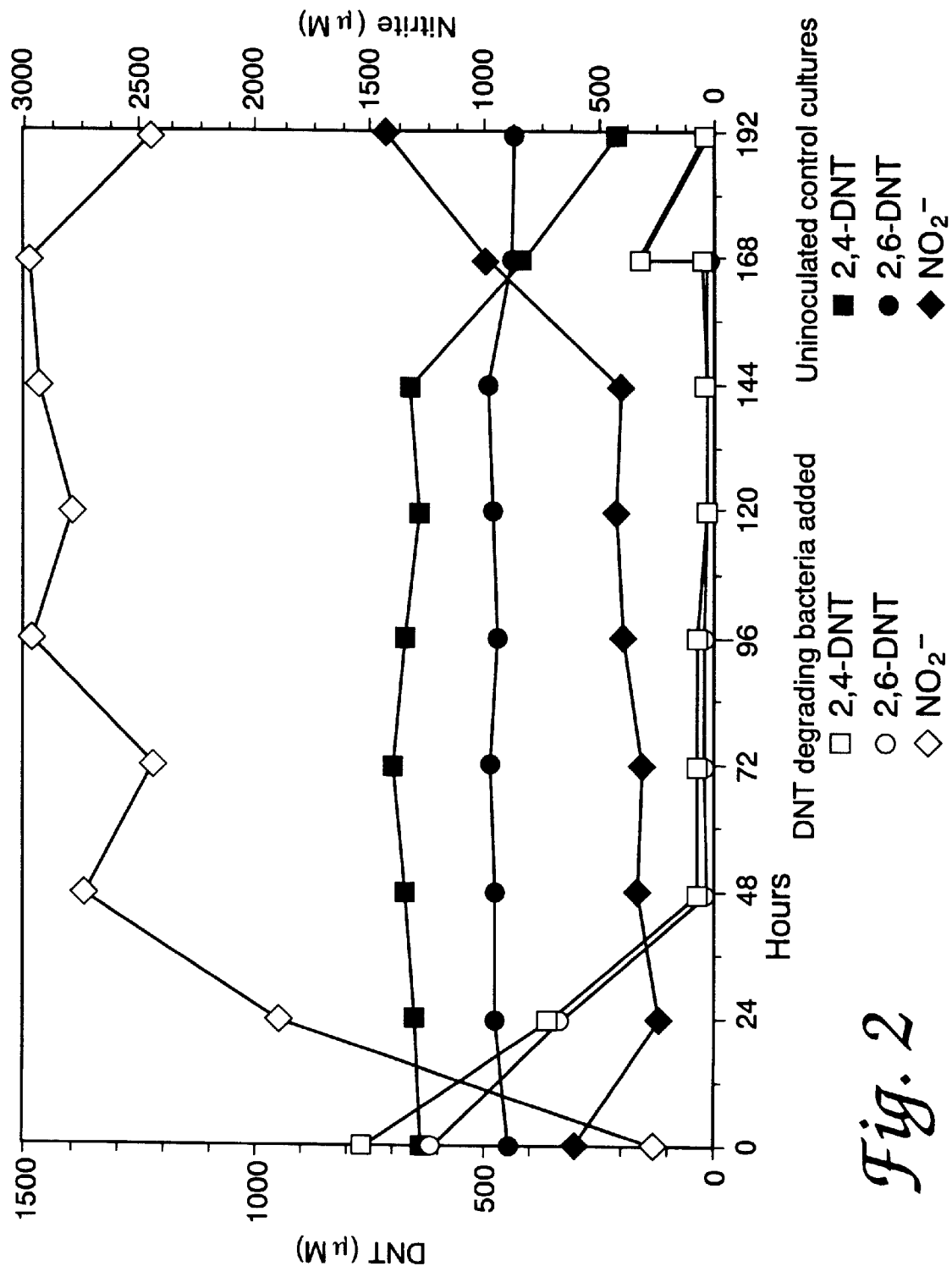
FIG. 2 shows the simultaneous removal of 2,4-DNT and 2,6-DNT in a batch soil slurry reactor using previously contaminated soil.

Simultaneous Removal of 2,4-DNT and 2,6-DNT in Batch Soil Slurry Reactor Using Previously Contaminated Soil The invention was tested in soil slurries that were made from soil collected from a site contaminated during munitions manufacture for WWII. When prepared as a 10% (w/v) soil slurry the resulting slurry contained 650 $\mu$M 2,4-DNT and 450 $\mu$M 2,6-DNT. No other carbon or nitrogen sources were provided. Triplicate cultures containing either mixtures of JS872 and JS863 or JS922 (approximately $10^7$ added cells/ml) were incubated at 30° C. with shaking at 200 rpm. The bacteria removed all DNT from the aqueous phase within 2 days, with stoichiometric release of nitrite (within 5 days at $10^5$ cells/ml). 2,4-DNT removal was seen in uninoculated control cultures several days after augmented cultures finished DNT removal, 2,6-DNT was not removed from the control cultures (FIG. 2). Results demonstrate that addition of specific DNT degrading strains to contaminated soils that may contain a 2,4-DNT degrading population can greatly enhance biodegradation of 2,4-DNT. Addition of 2,6-DNT degrading strains is essential for efficient degradation of 2,6-DNT.

EXAMPLE III

Simultaneous Removal of 2,4-DNT and 2,6-DNT in a Draw and Fill Soil Slurry Reactor Using Previously Contaminated Soil.

Experiments with aged field-contaminated soil were conducted in a bench scale slurry reactor. The reactor was filled with 600 ml of a 10% (w/v) soil slurry in phosphate buffer (20 mM, pH 7.0). The soil was from the former TNT-manufacturing plant at Hessisch Lichtenau, Germany. It consisted of equal parts by weight of the dried, sieved clay plus silt and sand fractions and contained 3.6 g of 2,4-DNT per kg of soil and 2.5 g of 2,6-DNT per kg soil. The organic content was 7.8% of dry weight. The inoculum consisted of a mixture of 5 ml each of strains JS872, JS863 and JS922 (2.5, 3.4 and 3.5 mg protein per ml, respectively). Initial DNT concentrations in the soil slurry totalled approximately 1 mM. Within 30 h of inoculation, the 2,4-DNT was degraded to a residual concentration in the slurry of approximately 28 $\mu$M, 2,6-DNT was degraded to 23 $\mu$M within 46 h. Two moles of nitrite were released per mole of DNT consumed, which clearly indicated that the DNT was degraded by the oxidative pathway used for mineralization. When levels of both isomers of DNT reached 20 $\mu$M, 90% of the slurry was removed and the reactor was refilled with fresh buffer and soil. Nine draw and fill cycles were completed in 600 h of operation. The length of time for completion of each cycle remained roughly constant throughout the run. Oxygen usage at 30° C. averaged 97 $\mu$g-$O_2$ per liter per minute and oxygen concentrations in the reactors remained above 2.5 mg/L throughout the experiment.

The time required to complete the cycles doubled when temperature was reduced from 30° C. to 24° C. Doubling the soil concentration of the slurry lengthened the time required for degradation proportionally. No additional bacteria or nutrients were added after the beginning of the experiment. The fact that reinoculation was not required indicated that the bacteria grew on DNT in a self-sustaining process.

Extended incubation of the soil slurry at 30° C., with agitation for 8 days reduced the residual concentrations of 2,4- and 2,6-DNT to 8 and 12 mg/kg. The concentration of 2,6-DNT removed from the soil slurries was approximately double the concentration that completely inhibits growth of bacteria in aqueous cultures.

EXAMPLE IV

Simultaneous Mineralization of 2,4-DNT and 2,6-DNT in Aged Contaminated Soil.

Mineralization experiments with aged contaminated soil in a 10% slurry (w/v) were conducted in a 2 L slurry bioreactor. The soil was also from Hessisch Lichtenau. The inoculum was a 200 ml aliquot from the reactor in Example III. The reactor contained approximately 570 mg 2,4-DNT and 390 mg 2,6-DNT from the soil and 40 $\mu$Ci radiolabelled DNT (0.43 mg 2,4-DNT, 0.14 mg 2,6-DNT, each isomer added individually in separate sequential experiments). Experiments with radiolabelled DNT were designed to provide rigorous evidence for the destruction of the contaminants. In each experiment, all of the radiolabelled DNT added and 99% of the unlabelled DNT from the soil was degraded. Almost 60% of the initial radiolabel was recovered as $^{14}CO_2$. The high level of mineralization taken with the stoichiometric release of nitrite clearly indicates that complete degradation of DNT occurs in the aerobic soil slurry reactor without accumulation of reduced byproducts.

EXAMPLE V

Simultaneous Removal of 2,4-DNT and 2,6-DNT in a Bench Scale Fluidized Bed Biofilm Reactor by a Mixed Culture of DNT-degradinq Strains A mixed culture of DNT-degrading strains was grown in a chemostat (250 ml working volume) for 6 months. The mixed culture consisted of a 2,4-DNT degrading strain, 19 2,6-DNT degrading strains and a 6-month-old 2,6-DNT enrichment culture derived from a mixture of DNT-contaminated industrial waste sludges, soils, and groundwaters. The chemostat was provided a mixture of 2,4-and 2,6-DNT (81 and 1,3 mg/L in the influent) as the sole carbon, nitrogen and energy source and operated at dilution rates from 0.01 to 0.05 during the 6 month period.

At the end of 6 months, 25 ml of the chemostat culture was used to inoculate a 1.5 L volume water jacketed fluidized bed reactor vessel with an inner diameter of 5.2 cm (Bioengineering, Wald ZH, Switzerland). The fluidized bed consisted of 0.74 kg of acid washed Ottawa sand (Ø0.425–0.595 mm). The bottom of the reactor was filled with 3 mm stainless steel balls to facilitate flow distribution. Temperature in the reactor was maintained at 20° C. pH was controlled to 7±0.1 by automatic addition of NaOH/KOH (1 M each) and phosphoric acid (10% v/v). Dissolved oxygen was monitored at the top of the fluidized bed and was maintained higher than 4.5 mg/L. A peristaltic pump delivered air to the recirculation line for aeration. Recirculation flow through the bed was maintained with a centrifugal pump at 1.5–1.6 L/min resulting in approximately 40% bed expansion. The fluidized bed reactor was operated at hydraulic retention times (HRT) of 12.5, 6.3, 3.1 1.5 and 0.75 h, in turn. For each HRT, steady-state was assumed when the concentrations of 2,4 and 2,6-DNT in the effluent varied less than 20% over a period of 3 days. Feed and recirculation lines were of stainless steel and glass. The feed was prepared sterile in 1 50-L stainless steel barrels and consisted of 2,4-DNT (40 mg/L), 2,6-DNT (10 mg/L), and $H_3PO_4$ (70 mg/L) in tap water. The feed solution was delivered to the FBBR recirculation line with a peristaltic pump.

Nitrate as well as nitrite was recovered because of the action of nitrite oxidizing bacteria present in the bioreactor. The sum of the nitrogen recovered as nitrite and nitrate represented greater than 90% of theoretical nitrogen released from DNT. Allowing for nitrogen used for growth, the total nitrogen released was stoichiometric with DNT degradation. Transient breakthrough of DNT occurred on days 57 and again on day 78 when the fluid bed was allowed to settle. Upon resumption of aeration and circulation a significant amount of biomass was washed out, however performance was recovered within 4 days.

Subsequent to the operation with DNT in tapwater, 190 L of groundwater from a contaminated site was supplied to the bioreactor as the sole influent. The groundwater contained 2,4-DNT (2.1 mg/L), 2,6-DNT (1.6 mg/L), 2-nitrotoluene (2.5 mg/L), and 4-nitrotoluene (1.7 mg/L). After 10 days operation at an HRT of 3 h, removal was the nitrotoluenes was 99.6, 62, 98 and 99.5%. The results indicate that bacteria able to degrade 2-nitrotoluene and 4-nitrotoluene can coexist with the DNT degrading biomass and extend the approach to include mixtures of mononitrotoluenes with DNT.

EXAMPLE VI

Figure 3:
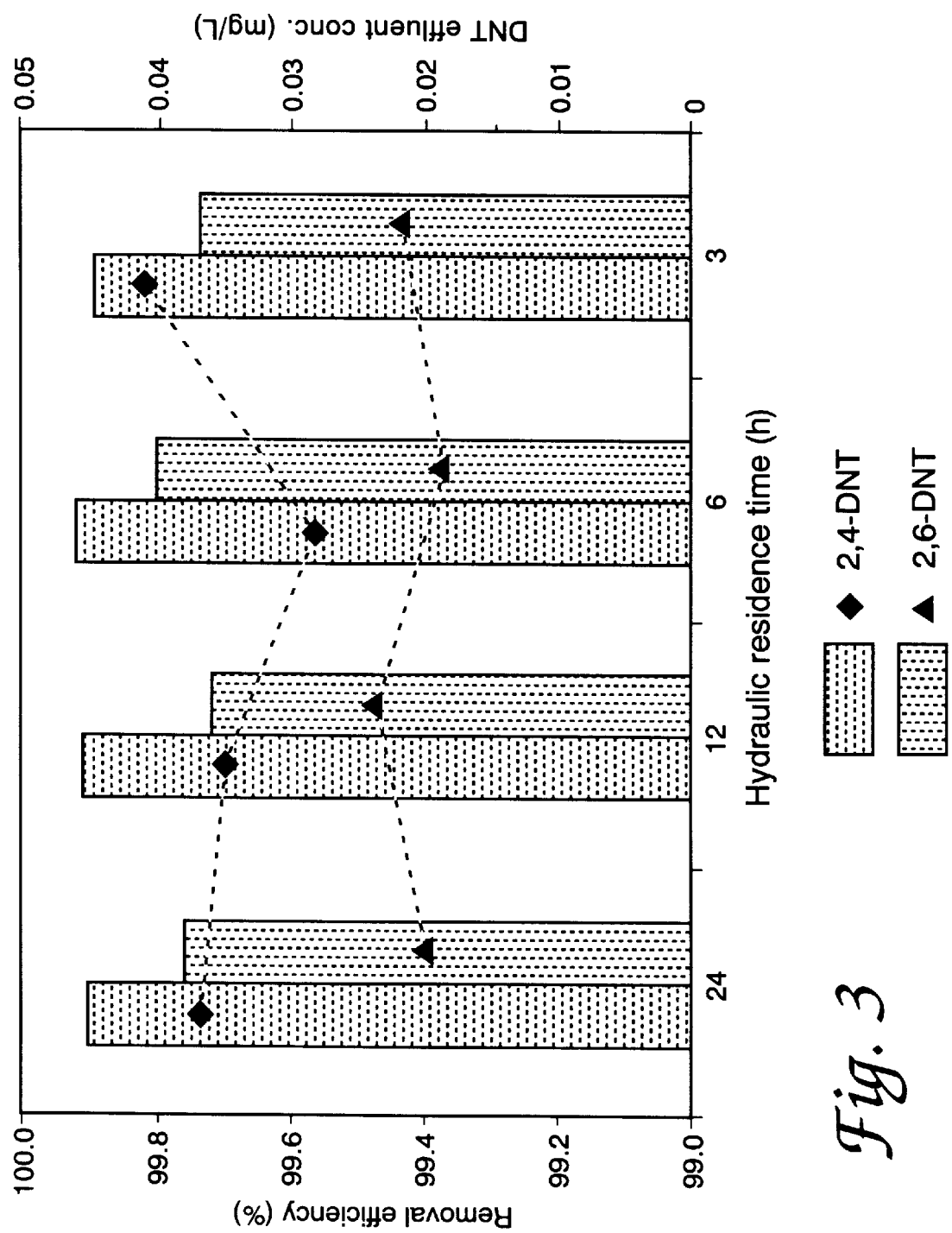
FIG. 3 shows the removal efficiencies in percentage of inflowing medium and the resulting effluent DNT concentrations at hydraulic residence times of 24, 12, 6, and 3 h.

Simultaneous Removal of 2,4-DNT and 2,6-DNT in a Bench Scale Fluidized Bed Biofilrn Reactor by a dual-degradinq Strain A pure culture of JS921, a DNT degrading strain that can grow on both isomers of DNT was used to inoculate the fluidized bed reactor described above in Example V. All operating parameters were the same except that the reactor was operated at HRT of 24, 12, 6, and 3 h, in turn. To maintain axenic conditions, the feed was prepared sterile in 20 L carboys. FIG. 3 shows the removal efficiencies in percentage of inflowing medium and the resulting effluent DNT concentrations at hydraulic residence times of 24, 12,6, and3h.

Various modifications may be made to the invention as described without departing from the spirit of the invention or the scope of the appended claims.

We claim:

1. A method for biodegrading dinitrotoluene present as a contaminant in a sample, comprising the steps of (a) providing a sample comprising dinitrotoluene; (b) adding to the sample a mixed culture of bacteria which degrade and use as a carbon and nitrogen source both the 2,4-dinitrotoluene isomer and the 2,6-dinitrotoluene isomer in the sample under aerobic conditions, said mixed culture consisting of bacterial strains JS872 and JS922; (c) producing aerobic conditions in the sample; and (d) maintaining the aerobic conditions in the sample for a time sufficient for the bacteria to degrade the dinitrotoluene.

2. A method for biodegrading dinitrotoluene present as a contaminant in a sample, comprising the steps of (a) providing a sample comprising dinitrotoluene; (b) adding to the sample a mixed culture of bacteria which degrade and use as a carbon and nitrogen source both the 2,4-dinitrotoluene isomer and the 2,6-dinitrotoluene isomer in the sample under aerobic conditions, said mixed culture consisting of bacterial strains JS872, JS863 and JS922; (c) producing aerobic conditions in the sample; and (d) maintaining the aerobic conditions in the sample for a time sufficient for the bacteria to degrade the dinitrotoluene.

* * * * *